(12) United States Patent
Galasso et al.

(10) Patent No.: US 8,676,601 B2
(45) Date of Patent: *Mar. 18, 2014

(54) DEVICE AND METHOD FOR AUTOMATIC DATA ACQUISITION AND/OR DETECTION

(71) Applicant: Abbott Diabetes Care Inc., Alameda, CA (US)

(72) Inventors: John R. Galasso, St. Helena, CA (US); Scott Dalton, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,562

(22) Filed: Apr. 8, 2013

(65) Prior Publication Data

US 2013/0297334 A1    Nov. 7, 2013

Related U.S. Application Data

(63) Continuation of application No. 13/400,026, filed on Feb. 17, 2012, now Pat. No. 8,417,545, which is a continuation of application No. 12/031,664, filed on Feb. 14, 2008, now Pat. No. 8,121,857.

(60) Provisional application No. 60/890,154, filed on Feb. 15, 2007.

(51) Int. Cl.
*G06Q 10/00* (2012.01)
*G06Q 50/00* (2012.01)

(52) U.S. Cl.
USPC .................................. 705/2; 705/3; 600/300

(58) Field of Classification Search
USPC .......................................... 705/2–3; 600/300
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |

(Continued)

FOREIGN PATENT DOCUMENTS

| | | |
|---|---|---|
| CA | 2399887 | 8/2006 |
| CA | 2268483 | 1/2007 |

(Continued)

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

(Continued)

*Primary Examiner* — Luke Gilligan
(74) *Attorney, Agent, or Firm* — Jackson & Co., LLP

(57) ABSTRACT

Methods and devices for providing diabetes management including automatic time acquisition protocol is provided.

20 Claims, 9 Drawing Sheets

(56) References Cited

U.S. PATENT DOCUMENTS

| | | |
|---|---|---|
| 4,425,920 A | 1/1984 | Bourland et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,673,322 A | 9/1997 | Pepe et al. |
| 5,711,001 A | 1/1998 | Bussan et al. |
| 5,711,861 A | 1/1998 | Ward et al. |
| 5,733,259 A | 3/1998 | Valcke et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,032,064 A | 2/2000 | Devlin et al. |
| 6,049,727 A | 4/2000 | Crothall |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,144,922 A | 11/2000 | Douglas et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,233,471 B1 | 5/2001 | Berner et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,544,212 B2 | 4/2003 | Galley et al. |
| 6,551,494 B1 | 4/2003 | Heller et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |

(56) References Cited

U.S. PATENT DOCUMENTS

| | | |
|---|---|---|
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,263 B2 | 5/2005 | Shin et al. |
| 6,895,265 B2 | 5/2005 | Silver |
| 6,925,393 B1 | 8/2005 | Kalatz et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,025,774 B2 | 4/2006 | Freeman et al. |
| 7,029,444 B2 | 4/2006 | Shin et al. |
| 7,041,068 B2 | 5/2006 | Freeman et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,267,665 B2 | 9/2007 | Steil et al. |
| 7,276,029 B2 | 10/2007 | Goode, Jr. et al. |
| 7,299,082 B2 | 11/2007 | Feldman et al. |
| 7,310,544 B2 | 12/2007 | Brister et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,424,318 B2 | 9/2008 | Brister et al. |
| 7,448,996 B2 * | 11/2008 | Khanuja et al. ............... 600/300 |
| 7,460,898 B2 | 12/2008 | Brister et al. |
| 7,467,003 B2 | 12/2008 | Brister et al. |
| 7,471,972 B2 | 12/2008 | Rhodes et al. |
| 7,476,827 B1 | 1/2009 | Bhullar et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2002/0019022 A1 | 2/2002 | Dunn et al. |
| 2002/0042090 A1 | 4/2002 | Heller et al. |
| 2002/0053523 A1 | 5/2002 | Liamos et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0064068 A1 | 4/2004 | DeNuzzio et al. |
| 2004/0073266 A1 | 4/2004 | Haefner et al. |
| 2004/0102683 A1 | 5/2004 | Khanuja et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0267300 A1 | 12/2004 | Mace |
| 2005/0004439 A1 | 1/2005 | Shin et al. |

(56) References Cited

U.S. PATENT DOCUMENTS

| | | |
|---|---|---|
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0038332 A1 | 2/2005 | Saidara et al. |
| 2005/0038680 A1 | 2/2005 | McMahon |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0123449 A1* | 6/2005 | Harada et al. ............... 422/68.1 |
| 2005/0131346 A1 | 6/2005 | Douglas |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0281234 A1 | 12/2005 | Kawamura et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0222566 A1 | 10/2006 | Brauker et al. |
| 2006/0224109 A1 | 10/2006 | Steil et al. |
| 2006/0229512 A1 | 10/2006 | Petisce et al. |
| 2006/0247508 A1 | 11/2006 | Fennell |
| 2006/0272652 A1 | 12/2006 | Stocker et al. |
| 2007/0016381 A1 | 1/2007 | Kamath et al. |
| 2007/0027381 A1 | 2/2007 | Stafford |
| 2007/0033074 A1 | 2/2007 | Nitzan et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0154513 A1 | 6/2008 | Kovatchev et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0306368 A1 | 12/2008 | Goode et al. |

(56) References Cited

U.S. PATENT DOCUMENTS

| | | |
|---|---|---|
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0105636 A1 | 4/2009 | Hayter et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| CN | 1710876 | 12/2005 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1669020 | 6/2006 |
| EP | 1729128 | 12/2006 |
| EP | 1288653 | 6/2011 |
| WO | WO-96/25089 | 8/1996 |
| WO | WO-96/35370 | 11/1996 |
| WO | WO-00/49940 | 8/2000 |
| WO | WO-00/59370 | 10/2000 |
| WO | WO-01/52935 | 7/2001 |
| WO | WO-01/54753 | 8/2001 |
| WO | WO-02/16905 | 2/2002 |
| WO | WO-03/076893 | 9/2003 |
| WO | WO-03/082091 | 10/2003 |
| WO | WO-2006/026741 | 3/2006 |
| WO | WO-2006/086423 | 8/2006 |

OTHER PUBLICATIONS

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

(56) References Cited

OTHER PUBLICATIONS

Salehi, C., et al., "A Telemetry-Instrumentation System for Long-Term Implantable Glucose and Oxygen Sensors", *Analytical Letters*, vol. 29, No. 13, 1996, pp. 2289-2308.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Chinese Patent Application No. 200880005149.1, Notification of Granting a Patent Right for an Invention mailed Jun. 21, 2013.

Chinese Patent Application No. 200880005149.1, Original Language and English Translation of Office Action mailed Aug. 17, 2011.

Chinese Patent Application No. 200880005149.1, Original Language and English Translation of Office Action mailed Dec. 3, 2012.

Chinese Patent Application No. 200880005149.1, Original Language and English Translation of Office Action mailed Feb. 16, 2012.

Chinese Patent Application No. 200880005149.1, Original Language and English Translation of Office Action mailed Jul. 29, 2010.

PCT Application No. PCT/US2008/054165, International Preliminary Report on Patentability and Written Opinion of the International Searching Authority mailed Aug. 27, 2009.

PCT Application No. PCT/US2008/054165, International Search Report and Written Opinion of the International Searching Authority mailed Jun. 5, 2008.

Russian Patent Application No. 2009134334, Original Language and English Translation of Office Action mailed Feb. 7, 2012.

U.S. Appl. No. 12/031,664, Advisory Action mailed Oct. 19, 2010.

U.S. Appl. No. 12/031,664, Notice of Allowance Oct. 24, 2011.

U.S. Appl. No. 12/031,664, Office Action mailed Aug. 2, 2010.

U.S. Appl. No. 12/031,664, Office Action mailed Feb. 19, 2010.

U.S. Appl. No. 12/031,664, Office Action mailed Mar. 18, 2011.

U.S. Appl. No. 13/400,026, Notice of Allowance mailed Jan. 22, 2013.

U.S. Appl. No. 13/400,026, Office Action mailed Sep. 17, 2012.

\* cited by examiner

DEVICE AND METHOD FOR AUTOMATIC DATA ACQUISITION AND/OR DETECTION

RELATED APPLICATIONS

The present application is a continuation of U.S. patent application Ser. No. 13/400,026 filed Feb. 17, 2012, now U.S. Pat. No. 8,417,545, which is a continuation of U.S. patent application Ser. No. 12/031,664 filed Feb. 14, 2008, now U.S. Pat. No. 8,121,857, which claims priority under §35 U.S.C. 119(e) to U.S. provisional patent application No. 60/890,154 filed Feb. 15, 2007, entitled "Device And Method For Automatic Data Acquisition And/Or Detection", the disclosures of each of which are incorporated herein by reference for all purposes.

BACKGROUND

In diabetes management, there exist devices which allow diabetic patients to measure the blood glucose levels. One such device is a hand-held electronic meter such as blood glucose meters such as Freestyle® blood glucose monitoring system available from Abbott Diabetes Care Inc., of Alameda, Calif. which receives blood samples via enzyme-based test strips. Typically, the patient lances a finger or alternate body site to obtain a blood sample, applies the drawn blood sample to the test strip, and the strip is inserted into a test strip opening or port in the meter housing. The blood glucose meter converts a current generated by the enzymatic reaction in the test strip to a corresponding blood glucose value which is displayed or otherwise provided to the patient to show the level of glucose at the time of testing.

Such periodic discrete glucose testing helps diabetic patients to take any necessary corrective actions to better manage diabetic conditions. Presently available glucose meters have limited functionalities (for example, providing the glucose value measured using the test strip and storing the data for subsequent recall or display) and do not provide any additional information or capability to assist patients in managing diabetes.

SUMMARY

In accordance with the various embodiments of the present disclosure, there are provided methods and devices for detecting a predefined parameter associated with an operational condition of an analyte monitoring device, transmitting a request for time information in response to the predefined parameter detection, and receiving time information in response to the transmitted request.

These and other objects, features and advantages of the present disclosure will become more fully apparent from the following detailed description of the embodiments, the appended claims and the accompanying drawings.

DETAILED DESCRIPTION

As described below, within the scope of the present disclosure, there are provided user interface features associated with the operation of the various components or devices in a therapy management system such as automatic time change based functions, automatic expiration date detection on test strips, for example, synchronization of the components in the therapy management system, user interface changes based on the user configuration, notification functions for programmable events associated with the therapy management, and voice enabled communication between devices in the therapy management system.

Figure 1:
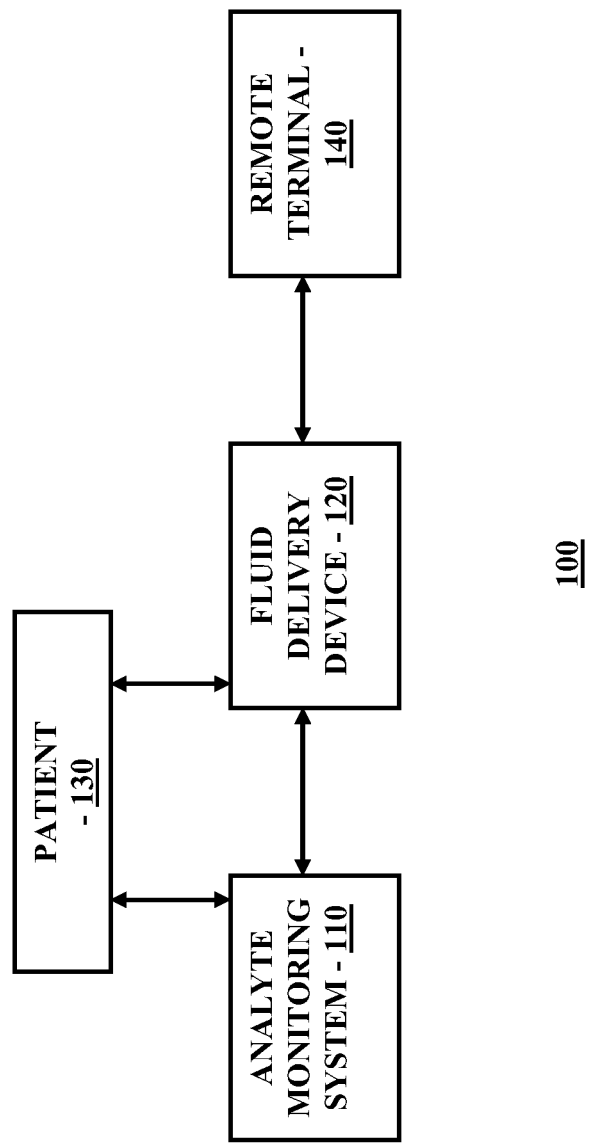
FIG. 1 is a block diagram illustrating a therapy management system for practicing one embodiment of the present disclosure.

FIG. 1 is a block diagram illustrating a therapy management system for practicing one embodiment of the present disclosure. Referring to FIG. 1, the therapy management system 100 includes an analyte monitoring system 110 operatively coupled to a fluid delivery device 120, which may be in turn, operatively coupled to a remote terminal 140. As shown in the Figure, the analyte monitoring system 110 is, in one embodiment, coupled to the patient 130 so as to monitor or measure the analyte levels of the patient. Moreover, the fluid delivery device 120 is coupled to the patient using, for example, an infusion set and tubing connected to a cannula (not shown) that is placed transcutaneously through the skin of the patient so as to infuse medication such as, for example, insulin, to the patient.

Referring to FIG. 1, the analyte monitoring system 110 in one embodiment may include one or more analyte sensors subcutaneously positioned such that at least a portion of the analyte sensors are maintained in fluid contact with the patient's analytes. The analyte sensors may include, but are not limited to short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the fluid delivery device 120 and/or the remote terminal 140 for further data processing and analysis.

In one aspect, each of the one or more receiver devices of the analyte monitoring system 110 and the fluid delivery device 120 includes a user interface unit which may include a display unit, an audio output unit such as, for example, a speaker, or any other suitable user interface mechanism for displaying or informing the user of such devices.

The transmitter units of the analyte monitoring system 110 may in one embodiment be configured to transmit the analyte related data substantially in real time to the fluid delivery device 120 and/or the remote terminal 140 after receiving it from the corresponding analyte sensors such that the analyte level such as glucose level of the patient 130 may be monitored in real time. In one aspect, the analyte levels of the patient may be obtained using one or more of discrete blood glucose testing devices such as blood glucose meters that employ glucose test strips, or continuous analyte monitoring systems such as continuous glucose monitoring systems. In a further embodiment, the analyte monitoring system 110 may include a blood glucose meter such as Freestyle® and Precision meters available from Abbott Diabetes Care Inc., of Alameda Calif. The blood glucose meter may be used to calibrate the sensors in the analyte monitoring system 110. Exemplary analyte systems that may be employed are described in, for example, U.S. Pat. Nos. 6,134,461, 6,175, 752, 6,121,611, 6,560,471, 6,746,582, and elsewhere, the disclosures of which are herein incorporated by reference.

Analytes that may be monitored, determined or detected in the analyte monitoring system 110 include, for example, acetyl choline, amylase, amyln, bilirubin, cholesterol, chorionic gonadotropin, creatine kinase (e.g., CK-MB), creatine, DNA, fructosamine, glucose, glutamine, growth hormones, hormones, ketones, lactate, measures for oxidative stress (such as 8-iso PGF2gamma), peroxide, prostate-specific antigen, prothrombin, RNA, thyroid stimulating hormone, and troponin. The concentration of drugs, such as, for example, antibiotics (e.g., gentamicin, vancomycin, and the like), biguanides, digitoxin, digoxin, drugs of abuse, GLP-1, insulin, PPAR agonists, sulfonylureas, theophylline, thiazolidinediones, and warfarin, may also be determined.

Moreover, within the scope of the present disclosure, the transmitter units of the analyte monitoring system 110 may be configured to directly communicate with one or more of the remote terminal 140 or the fluid delivery device 120. Furthermore, within the scope of the present disclosure, additional devices may be provided for communication in the analyte monitoring system 110 including additional receiver/data processing units, remote terminals (such as a physician's terminal and/or a bedside terminal in a hospital environment, for example).

In addition, within the scope of the present disclosure, one or more of the analyte monitoring system 110, the fluid delivery device 120 and the remote terminal 140 may be configured to communicate over a wireless data communication link such as, but not limited to radio frequency (RF) communication link, Bluetooth® communication link, infrared communication link, or any other type of suitable wireless communication connection between two or more electronic devices, which may further be uni-directional or bi-directional communication between the two or more devices. Alternatively, the data communication link may include wired cable connections such as, for example, but not limited to RS232 connection, USB connection, or serial cable connection.

The fluid delivery device 120 may include in one embodiment, but not limited to, an external infusion device such as an external insulin infusion pump, an implantable pump, a pen-type insulin injector device, a patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Referring back to FIG. 1, in one embodiment, the analyte monitoring system 110 includes a strip port configured to receive a test strip for capillary blood glucose testing. In one aspect, the glucose level measured using the test strip may in addition, be configured to provide periodic calibration of the analyte sensors of the analyte monitoring system 110 to assure and improve the accuracy of the analyte levels detected by the analyte sensors.

Referring yet again to FIG. 1, in one embodiment of the present disclosure, the fluid delivery device 120 may be configured to include a voice signal activation/generation unit for voice communication with the remote terminal 140 configured as a voice device such as a mobile telephone, a voice enabled personal digital assistant, a Blackberry device, or the like. For example, in one embodiment, the communication between the fluid delivery device 120 and the remote terminal 140 may be voice based such that the information or data output to the user from the fluid delivery device 120 is configured to be transmitted to the user's telephone. In turn, the fluid delivery device 120 may additionally be configured to receive voice commands from the remote terminal 140 configured as a telephone or any other voice signal communication device (such as personal computers or PDAs with voice signal capabilities).

In this manner, in one embodiment, the user interface of the fluid delivery device 120 may be configured with the voice signal activation/generation unit such that, output information for the user is converted into a voice signal and transmitted to the voice signal enabled remote terminal 140. For example, when the fluid delivery device 120 detects an alarm condition, the fluid delivery device 120 is configured to initiate a telephone call to the user's telephone (remote terminal 140), and when the user picks up the telephone line, the user is provided with a voice signal representing the alarm condition.

In a further embodiment, for certain predetermined patient conditions, the fluid delivery device 120 may be configured to initiate a telephone call directly to a preprogrammed telephone number of a health care physician, a local hospital, or emergency medical care facilities, in addition to or instead of initiating a telephone call to the user of the fluid delivery device 120.

In addition, within the scope of the present disclosure, interaction and programming of the fluid delivery device 120 may be exclusively or partially exclusively performed over the user's telephone in voice communication with the fluid delivery device 120. That is, when the user wishes to calculate a carbohydrate bolus in the fluid delivery device 120, the user may dial a predetermined number using the user's telephone (remote terminal 140) to connect with the fluid delivery device 120, and the user may provide voice commands to the fluid delivery device 120 via the telephone connection between the user's telephone (remote terminal 140) and the fluid delivery device 120.

Figure 2:
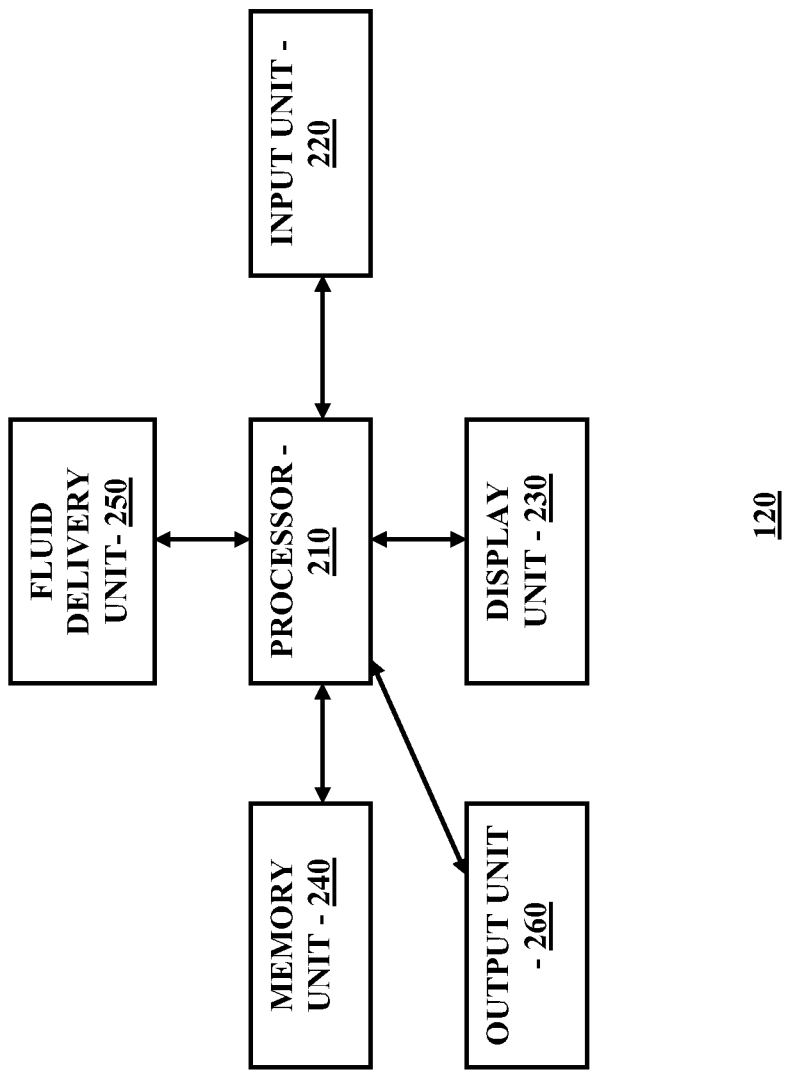
FIG. 2 is a block diagram of a fluid delivery device of FIG. 1 in one embodiment of the present disclosure.

FIG. 2 is a block diagram of a fluid delivery device of FIG. 1 in one embodiment of the present disclosure. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as safety measure and to provide redundancy in case of a single processor failure. Moreover, processing capabilities may be shared between multiple processor units within the fluid delivery device 120 such that pump functions and/or control may be performed faster and more accurately.

Referring back to FIG. 2, the input unit 220 operatively coupled to the processor 210 may include a jog dial key pad buttons, a touch pad screen, or any other suitable input mechanism for providing input commands to the fluid delivery device 120. More specifically, in case of a jog dial input device, or a touch pad screen, for example, the patient or user of the fluid delivery device 120 will manipulate the respective jog dial or touch pad in conjunction with the display unit 230 which performs as both a data input and output unit. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

In one embodiment, the alphanumeric representation displayed on the display unit 230 may be configured to be modified by the user of the fluid delivery device such that the size of the displayed number or character may be adjusted to suit the user's visual needs. For example, in one embodiment, the user may apply font size adjustment request via the input unit 220 to instruct the processor 210 to modify the size of the displayed number or character on the display unit 230. In one aspect, the font size may be increased or decreased for each character, value or word displayed on the display unit 230. Alternatively, the font size adjustment may be applied globally to all output settings, for example, under the control of the processor 210 such that the user setting of the size adjustment may be configured to apply to substantially all displayed values or characters on the display unit 230 of the fluid delivery device 120 (FIG. 1).

Moreover, referring back to FIG. 2, in a further aspect of the present disclosure, the relative size adjustment of the displayed character or value may be determined by the processor 210 so that the relative size adjustment may be implemented to the output display on the display unit 230. In this manner, depending upon the type or configuration of the display unit 230 (whether bit map or icon type display), in one embodiment, the display size adjustment may be implemented within the predetermined size restrictions for the respective value or character. For example, a 10% relative increase in the font size for display area designated for insulin dosage level may correspond to a 5% relative increase in the size of the display area designated for the insulin delivery time display. In one embodiment, the processor 210 may be configured to determine the relative size modification for each area of the display unit 230 based on the user inputted size adjustment values to appropriately apply the relative size differential adjustment.

In a further aspect, the processor 210 may be configured to temporarily increase the font size displayed on the display unit 230 based on the user input commands such that the user requested size modification on the display unit 230 may be implemented only for the displayed screen at the time the user input commands for size adjustment is received by the processor 210. In this manner, the processor may be configured to revert to the previously programmed display size settings for the display unit 230 when the user is no longer viewing the particular displayed screen from which the user has requested font size adjustment.

In addition, the user interface of the receiver unit of the analyte monitoring system 110 (FIG. 1) may be configured with similar size adjustment capabilities so as to allow the user to instruct the controller or processor of the analyte monitoring system 110 to appropriately adjust the size of the displayed character or value on the display unit of the analyte monitoring system 110.

In a further embodiment, the display unit 230 may be configured to display an indication or marker for the type of insulin or other medication being used by the fluid delivery device 120 such as, for example, Symlin and Byetta. Such a marker may, in one embodiment, be associated with a predefined icon or character for display on the display unit 230. In addition, within the scope of the present disclosure, the information associated with the displayed marker or indication may be stored in the memory unit 240 so that the user may retrieve this information as desired. In addition, an indication or a marker for shift work may be programmed in the fluid delivery device 120 (FIG. 1) such that shift workers using the fluid delivery device 120 may align days and nights upon command based on the markers.

For example, if a user worked nightshifts on Mondays and Tuesdays and dayshifts on Thursdays and Fridays, this daily work pattern information may be stored, identified or marked in the fluid delivery device 120 to provide additional data management functionalities and a more robust therapy analysis. For example, meal times such as breakfasts, for example, at 8 pm on Monday and 9 pm on Tuesday (during the nightshifts) may be aligned with the breakfasts at 7 am on Thursday and 8 am on Friday. In this manner, the user may conveniently access meal (e.g., breakfast) related data and associated therapy information in conjunction with the operation of the fluid delivery device 120. This may assist the user in improving upon the user's diet such as the daily food intake.

Referring to FIG. 2, the output unit 260 operatively coupled to the processor 210 may include an audible alarm or alarms including one or more tones and/or preprogrammed or programmable tunes or audio clips, or vibratory alert features having one or more pre-programmed or programmable vibratory alert levels.

In addition, in one embodiment of the present disclosure, each alert event or alarm event may be programmed with combined notification features such that, depending upon the level of importance associated with each alert or alarm, a combination of vibratory, audible, or displayed indications may be provided to the user using the display unit 230 in combination with the output unit 260.

For example, the processor 210 may be configured to provide combined vibratory and increasingly audible alerts on the output unit 260 in addition to intermittently flashing background light on the display unit 230 for one or more predetermined alarms that require immediate user attention. An example may include unexpected pressure increase in the infusion tubing which may indicate an occlusion or other undesirable condition that the user should be immediately notified. The processor 210 may be configured such that the alarm or alert may be automatically reasserted within a predetermined time period in the event the associated alarm or alert condition has not been cleared by the user. In addition, each alert/alarm feature may be individually programmed to include a wide selection of tones, audible levels, vibratory strength, and intensity of visual display.

In a further aspect, the fluid delivery device 120 may be configured to provide an alarm or alert indication associated with a change in temperature. That is, when the fluid delivery device 120 which contains the insulin (for example, in a reservoir) experiences a rise or drop in temperature, such change in the temperature may have an adverse effect on the insulin contained within the device 120. Accordingly, a temperature sensor may be coupled to the processor 210 of the fluid delivery device 120 to detect the operating condition of the fluid delivery device 120 and to notify the user of changes in the temperature, when, for example, the temperature change reaches a predetermined threshold level that may potentially have an adverse impact upon the efficacy of the insulin being delivered.

Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other type of data storage unit that is configured to store data as well as program instructions for access by the processor 210 and execution to control the fluid delivery device 120 and/or to perform data processing based on data received from the analyte monitoring system 110, the remote terminal 140, the patient 130 or any other data input source.

Figure 3:
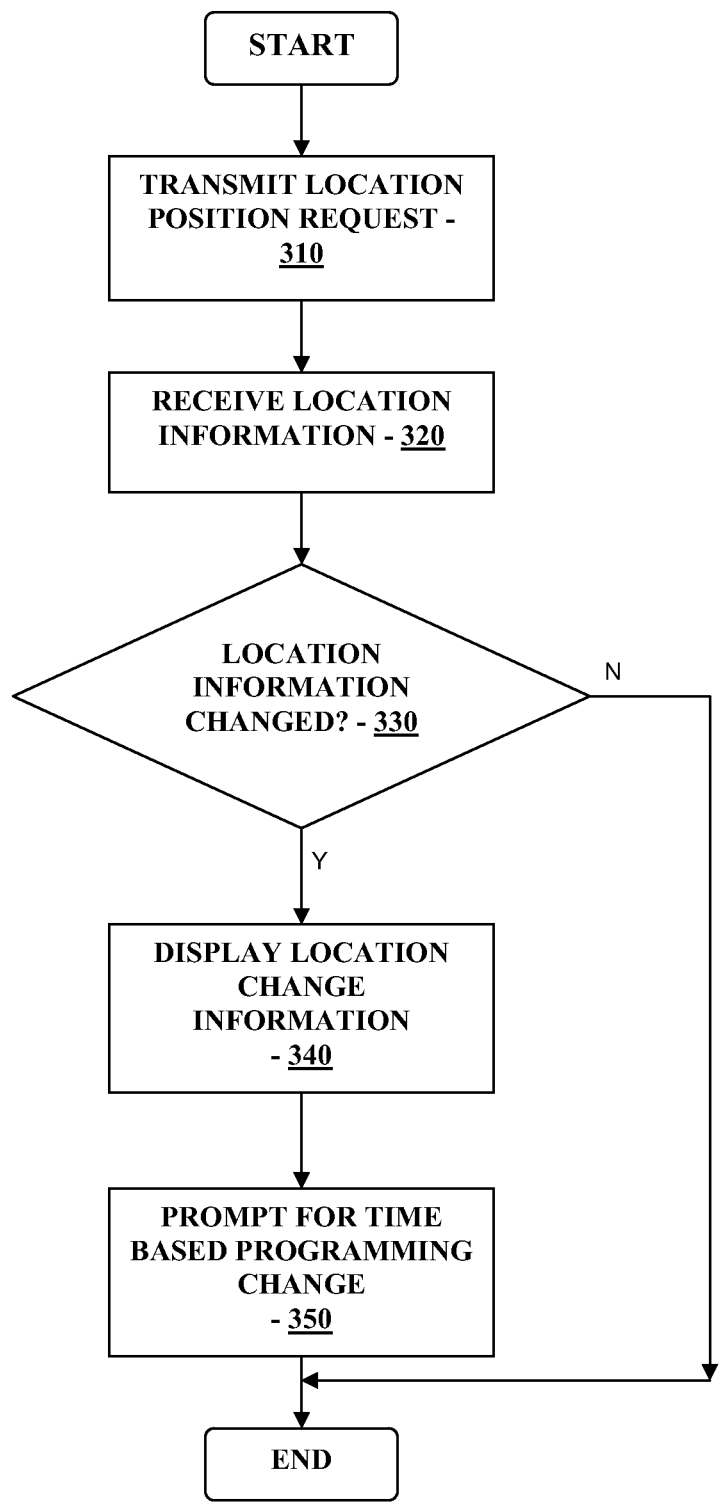
FIG. 3 is a flowchart illustrating the time zone detection procedure in the therapy management system in one embodiment of the present disclosure.

FIG. 3 is a flowchart illustrating the time zone detection procedure in the therapy management system in one embodiment of the present disclosure. Referring to FIG. 3, the fluid delivery device 120 (FIG. 1) may be configured to transmit a location position request (310) to for example, a global positioning system (GPS). Thereafter, the location information is received (320) by the processor 210 of the fluid delivery device 120. The processor 210 is further configured to determine whether the location information has changed (330). That is, the processor 210 in one embodiment is configured to compare the receive location information which may include a current time zone information associated with the location of the fluid delivery device 120, with the previously stored and operating time zone information in the fluid delivery device 120 in operation.

Referring back, if it is determined that the location information has not changed, then the routine terminates. On the other hand, if it is determined that the fluid delivery device location information has changed, then, the location change information is output (340) to the user on the display unit 230, for example. Thereafter, the processor 210 may be configured to generate a user prompt or notification to modify the time zone information (350) of the fluid delivery device 120 such that it is updated to the new location where the fluid delivery device 120 is operating.

For example, when the fluid delivery device 120 is programmed with predetermined basal profiles and/or bolus functions that are time based and associated with an internal clock of the fluid delivery device 120, it may be desired to modify some or all of the time based insulin delivery profiles programmed in the fluid delivery device 120 so as to correspond to the location of the fluid delivery device 120. More specifically, if a user is traveling from a first location to a second location in which one or more time zones are traversed, e.g., by way of example from San Francisco to Paris, given the time difference, the meal times, and sleep times, for example, will change. In this case, it may be desirable to modify the preprogrammed time based insulin delivery profiles so that they are synchronized with the user events such as meals and sleep times.

Referring back to FIG. 3, in one embodiment, the user responds to the time based programming change prompt provided by the processor 210, then the processor 210 may be configured in one embodiment, to propagate the time change associated with the preprogrammed insulin delivery profile and notify the user to confirm the changes, prior to implementing the modification to the delivery profiles and any associated alerts or notifications. For example, in the case where the user has programmed to be alerted at a particular time of day, e.g., noon each day, for a bolus determination prior to lunch, the processor 210 in one embodiment is configured to either modify the internal clock of the fluid delivery device 120 or alternatively, modify the programmed alert for bolus determination so as to correspond to the new location of the user and the fluid delivery device 120.

In another embodiment, the fluid delivery device 120 may be configured to include a time zone detection unit, such as for example, the processor 210 may be configured to communicate with a geographical location change detection mechanism (e.g., an atomic clock) operatively coupled to the processor 210 for performing the time zone detection procedure as described above in conjunction with FIG. 3. In addition, the analyte monitoring system 110 may be configured to include a time zone detection unit as described above to automatically or based on a preprogrammed procedure, detect any location change associated with the analyte monitoring system 110. In this manner, the analyte monitoring system 110 may be configured to automatically or based on a preprogrammed procedure, implement modifications to functions associated with the operation of the analyte monitoring system 110 that are temporally associated with the time of day information.

Figure 4:
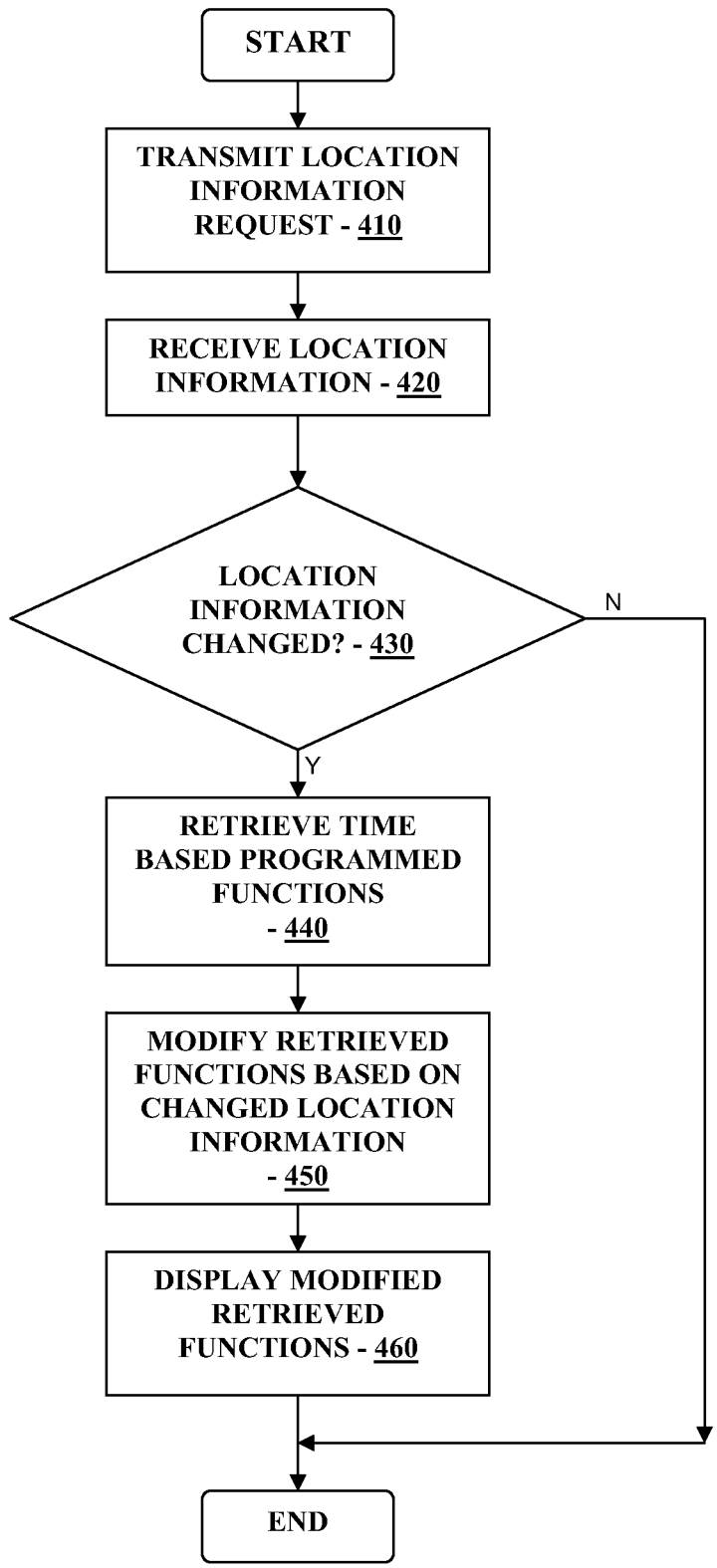
FIG. 4 is a flowchart illustrating the time zone detection procedure in the therapy management system in another embodiment of the present disclosure.

FIG. 4 is a flowchart illustrating the time zone detection procedure in the therapy management system in another embodiment of the present disclosure. Referring to FIG. 4, the fluid delivery device 120 (FIG. 1) may be configured to transmit a location position request (410) to for example, a global positioning system (GPS). Thereafter, the location information is received (420) by the processor 210 of the fluid delivery device 120. The processor 210 is further configured to determine whether the location information has changed (430). That is, the processor 210 in one embodiment is configured to compare the receive location information which may include a current time zone information associated with the location of the fluid delivery device 120, with the previously stored and operating time zone information in the fluid delivery device 120 in operation.

Referring back, if it is determined that the location information has not changed (330), then the routine terminates. On the other hand, if it is determined that the fluid delivery device location information has changed (330), then, the processor 210 in one embodiment is configured to retrieve one or more time based programmed functions (440) from the memory unit 240 of the fluid delivery device 120, for example.

Thereafter, the processor 210 may be further configured to modify the retrieved time based preprogrammed functions in accordance with the location change information received (450). Then, the modified retrieved functions are provided to the user (460) on the display unit 230, for example, to request confirmation of the time based adjustments, prior to the processor 210 executing the modified retrieved functions.

In addition, in one embodiment of the present disclosure, the fluid delivery device 120 may be configured to detect for daylight savings time and the processor 210 may be configured to either automatically execute the time change in the internal clock of the fluid delivery device, and/or provide a user notification to accept such time based change so that the operation of the fluid delivery device 120 performing time based programs are updated with any time based change in the insulin delivery system 120 operating environment.

Within the scope of the present disclosure, the fluid delivery device 120 may be configured to receive location information from any positioning system which provides updated time information based on location. The fluid delivery device 120 may be configured with a positioning transceiver that is configured to transmit location information requests to a satellite network, for example, and to receive the location information therefrom.

Alternatively, the fluid delivery device 120 may be configured to update its location information locally upon synchronization with another device operating in the local (or at the new location). This may include a host computer terminal connectable to the fluid delivery device 120 such as, for example, the remote terminal 140 (FIG. 1), the analyte monitoring system 110, or any other electronic device operating in the new location with communication capabilities with the fluid delivery device 120 such as a cellular telephone, a personal digital assistant, and the like.

In addition, within the scope of the present disclosure, the procedure and processes described in conjunction with FIGS. 3-4 associated with location change information and corresponding modification to the time based preprogrammed functions in the fluid delivery device 120 may be provided to the analyte monitoring system 110 such that the analyte monitoring system 110 is also configured to receive new location information and correspondingly perform modifications to any time based preprogrammed functions.

Figure 5:
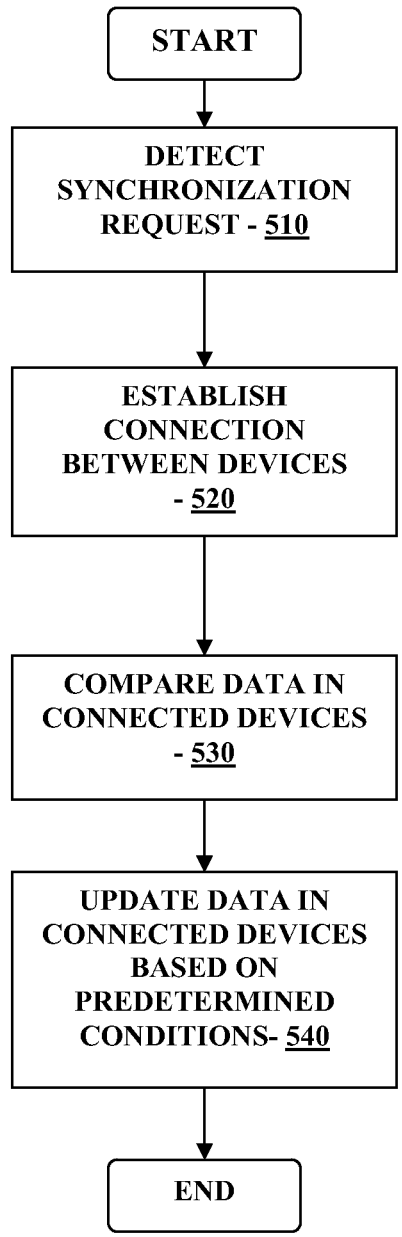
FIG. 5 is a flowchart illustrating the device synchronization procedure in the therapy management system in one embodiment of the present disclosure.

FIG. 5 is a flowchart illustrating the device synchronization procedure in the therapy management system in one embodiment of the present disclosure. Referring to FIG. 5, in one embodiment the fluid delivery device 120 (FIG. 1) may be configured to detect a synchronization request (510) from another device such as the remote terminal 140 or the analyte monitoring system 110 (FIG. 1). Thereafter, data communication connection is established (520) between the fluid delivery device 120 and the synchronization requesting device. In one embodiment, the fluid delivery device 120 is configured to verify the authenticity or identity of the device requesting synchronization, and upon synchronization approval, the fluid delivery device 120 is configured to establish communication with the synchronization requesting device.

In addition, within the scope of the present disclosure, the fluid delivery device 120 may be configured to periodically or at a predetermined time interval, establish communication connection with another device for synchronization. Alternatively, the fluid delivery device may be configured to attempt communication connection when another device for synchronization is detected within a predefined distance from the location of the fluid delivery device 120.

Referring back to FIG. 5, the fluid delivery device 120 is configured in one embodiment to transmit its programmed and operating settings to the connected device (530), and the connected device is configured to update and store the data received from the fluid delivery device 120 based on predetermined conditions (540). For example, the predetermined conditions may include a predefined set of rules associated with the type of data from the fluid delivery device 120 to be updated such as historical infusion related information, programmed functions in the fluid delivery device 120 such as bolus calculations, temporarily basal profiles, programmed basal profiles, insulin usage level, and any other information that is associated with the user.

In this manner, in one embodiment of the present disclosure, periodic synchronization of the fluid delivery device 120 settings and functions may be synchronized to another device so that when the user replaces the fluid delivery device 120, the new or upgrade fluid delivery device may be easily and readily programmed to the user's specification. The synchronization described above may be configured to be performed periodically at a regular interval such as, once a week, once per day, when certain predefined criteria are met such as when the devices are within a predetermined distance from each other, and/or upon user command.

In addition, within the scope of the present disclosure, the fluid delivery device 120 may be configured with any communication protocol which would allow data transfer between the fluid delivery device 120 and the synchronizing device. This may include, wired or wireless communication including for example, Bluetooth® protocol, 802.1x protocol, USB cable connection and the like.

Figure 6:
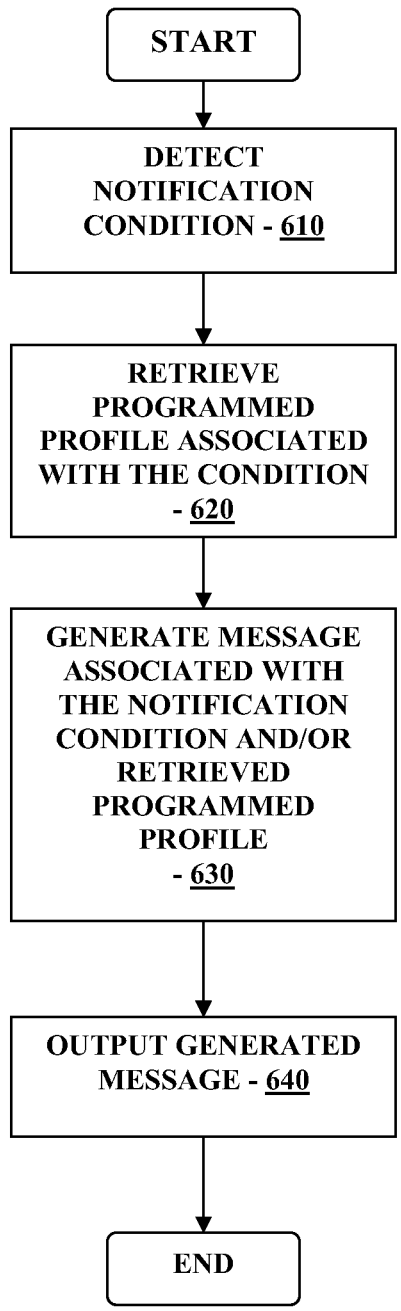
FIG. 6 is a flowchart illustrating device condition notification function in the therapy management system in one embodiment of the present disclosure.

FIG. 6 is a flowchart illustrating device condition notification function in the therapy management system in one embodiment of the present disclosure. Referring to FIG. 6 the fluid delivery device 120 may be configured to detect a notification condition (610). For example, the processor 210 may be configured to detect such notification conditions at a preprogrammed time interval (such as about every 24 hours, for example). Thereafter, the programmed profile associated with the condition is retrieved (620). An example of the programmed profile associated with the condition includes a reminder to start an overnight fast for the user.

Referring back to FIG. 6, the processor 210 in one embodiment is further configured to generate a message associated with the notification condition and/or the retrieved programmed profile (630), and, the generated message is provided to the user (640) on one or more of the display unit 230 or the output unit 260. In this manner, in one embodiment of the present disclosure, the fluid delivery device 120 may be programmed with automatic reminders for conditions to assist the user to improve insulin therapy management.

In one embodiment, the notification condition detection may be skipped and the processor 210 may be configured to retrieve the appropriate programmed profile associated with notification conditions based on the user programming of the fluid delivery device 120. Additionally, while a reminder for overnight fast is described as an example, any other therapy related reminders or device operating condition reminders may be programmed for execution by the processor 210 to remind the user. Examples of such reminders include, but are not limited to, infusion set replacement reminder, battery replacement reminder, data synchronization reminder, insulin replenishment reminder, glucose testing reminder, and the like. In addition, within the scope of the present disclosure, the procedure described in conjunction with FIG. 6 may be incorporated in the analyte monitoring system 110 for programming suitable automatic reminders such as, for example, sensor replacement reminder, sensor calibration reminder, and the like.

Figure 7:
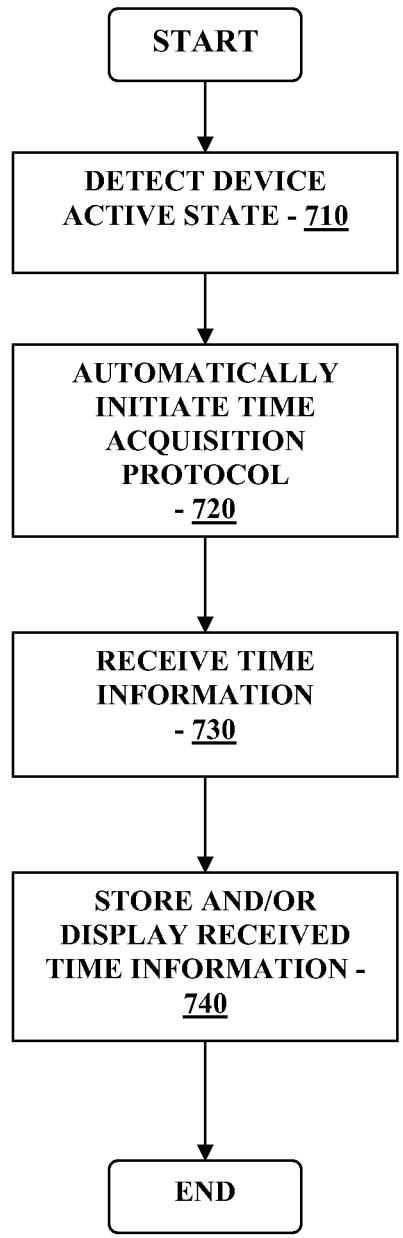
FIG. 7 is a flowchart illustrating automatic time information detection function incorporated in a medical device such as a blood glucose meter in one embodiment of the present disclosure.

FIG. 7 is a flowchart illustrating automatic time information detection function incorporated in a medical device such as a blood glucose meter of the analyte monitoring system 110 in one embodiment of the present disclosure. Referring to FIG. 7, when the medical device active state is detected (710)

for example, by the user initiated power on procedure of the medical device such as a blood glucose meter, a routine is called by the processor of the medical device to automatically initiate time acquisition protocol. That is, upon power on of the medical device, the device is automatically configured to perform time acquisition protocol to, among others, transmit request for time and/or date information to available communication channels, and upon receiving the information, to store, update and/or otherwise set and/or display the received or acquired time/date information in the medical device (720-740).

Referring back to FIG. 7, in one embodiment, the time information is received at step 730, and thereafter, the received time information is stored and/or displayed on a display unit of the medical device. In one aspect, the medical device is configured to update all previously stored time associated data (for example, blood glucose readings taken at certain times of the day (or week, month, or any other time period)). More specifically, in one embodiment, when the medical device such as the blood glucose meter is activated by the user, the processor or controller of the glucose meter is configured to enable or activate time/date receiver (for example, a communication component such as a radio frequency transceiver coupled to the processor of the glucose meter). The time/date receiver in one embodiment is configured to seek or acquire automatically, upon activation, time and date information from one or more available communication networks within range. For example, the time/date receiver may be configured to detect the time/date information from one or more radio frequencies on public, government, or private airwaves using AM band short frequency or FM band long wave frequency. Alternatively, as discussed above, current local time/date information may be received from global positioning satellites, as well as cellular telephone networks such as GSM, CDMA, AMPS, and the like within range of the time/date receiver in the medical device. Additionally, WiFi network may be used to receive the time/data information, if available and within range.

In this manner, in one embodiment, the medical device such as a blood glucose meter, may be configured to automatically acquire time information that is continuously broadcast on a frequency in which the antenna and the receiver of the blood glucose meter are configured to operate. Upon obtaining and verifying the time and date information, the internal clock function or component is updated or adjusted with the acquired time/date information and displayed to the user, for example.

In a further embodiment, the medical device such as a blood glucose meter may be configured to use GMT time as the reference time for all log entry (for example, for each blood glucose test performed) timestamps associated with each data stored in the medical device. Thereafter, the medical device may be configured to convert the stored GMT based time information for each log entry stored in the medical device to the local time based on the location of the medical device.

Figure 8:
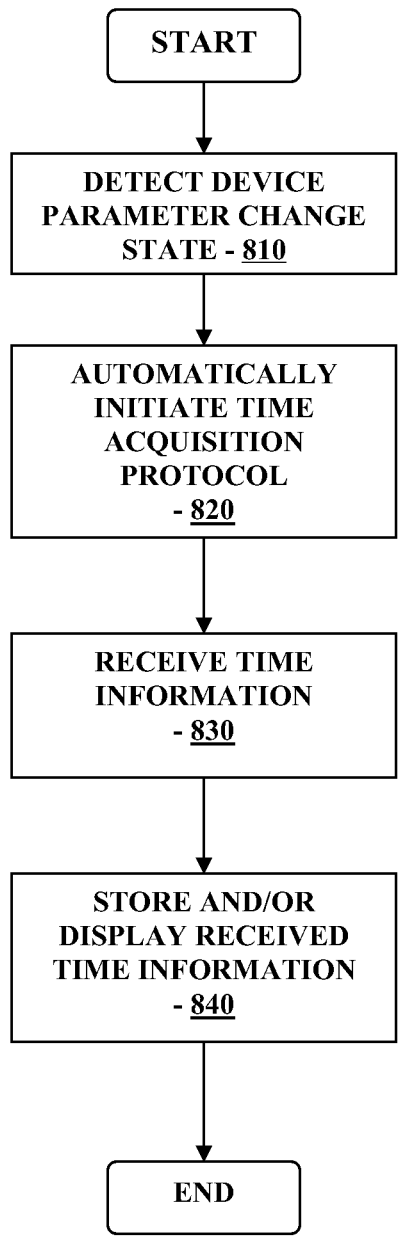
FIG. 8 is a flowchart illustrating automatic time information detection function incorporated in a medical device such as a blood glucose meter in another embodiment of the present disclosure.

FIG. 8 is a flowchart illustrating automatic time information detection function incorporated in a medical device such as a blood glucose meter in another embodiment of the present disclosure. Referring to FIG. 8, in one embodiment, the automatic time acquisition protocol is initiated based on a detection of one or more changed or preconfigured parameters associated with the medical device and/or the user of the medical device (810). For example, the device parameter may include a preconfigured time for periodically checking for time and date information (such as every 24 hours, 48 hours, or based on a programmed calendar such as to compensate for daylight savings time change).

Alternatively, the device parameter may include an environmental condition change associated with the medical device or the user, such as a detection of the medical device location such as during travel by air or a vehicle. That is, in one embodiment, the medical device may be configured to include an altimeter which is coupled to the processor of the medical device to detect a change in altitude of the medical device location for example, when the user of the medical device is traveling by air. In such a case, the medical device may be configured to initiate the time acquisition protocol to confirm or verify the time and date information of the medical device (820-840).

Further, the medical device may include an accelerometer which may be configured to initiate the automatic time acquisition protocol on the medical device when a predetermined threshold level of acceleration force is reached. Within the scope of the present disclosure, other parameters may be used in conjunction with the medical device to trigger the automatic time acquisition protocol on the medical device (820-840) such that, without user intervention, prompting, or initiating, the medical device is configured to automatically initiate time and date information acquisition routine. In addition, the functionality of the automatic time and date information acquisition may be incorporated in other medical devices such as infusion pumps, continuous glucose monitoring devices, heart rate monitors, and the like that are configured to maintain a time associated log of physiological data (such as glucose levels, insulin infusion rates, cardiac signal levels and so on) of a patient or a user.

Figure 9A:
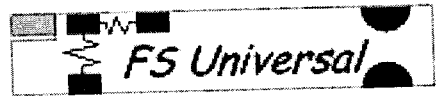
FIGS. 9A-9C illustrate embodiments of automatic expiration detection function on blood glucose meter test strips in accordance with one embodiment of the present disclosure.
Figure 9B:
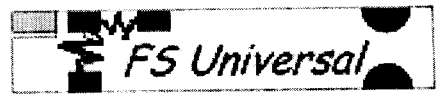
Figure 9C:

FIGS. 9A-9C illustrate embodiments of automatic expiration detection function on blood glucose meter test strips in accordance with one embodiment of the present disclosure. Presently, test strips for use with blood glucose meters are sold or made available in containers that include the expiration date information of the test strips contained therein. For diabetic patients or healthcare providers using glucose meters, it is important to check the expiration information of the test strip before testing for glucose levels so that the obtained results are accurate.

Referring to FIGS. 9A-9C, in one embodiment, test strips may be configured with predefined parameters to allow automatic expiration date detection of the test strip. In one aspect, resistance values are provided on the test strips such that when the test strip is inserted into the strip port of the blood glucose meter, the meter is configured to compare the detected resistance value to a stored value of resistance, and determine whether the inserted test strip has expired or not. More specifically, in one embodiment, using the resistance value on the test strip, the expiration date information may be coded, and the meter may be configured to detect the resistance value of the test strip and determine whether the test strip has expired.

In one aspect, the resistance value on the test strip may be controlled with the ink formulation on the wake up bar and/or patterns provided thereon. Silver, gold, carbon or any other suitable conductive material may be used to increase the resistance as may be desired. The blood glucose meter may be configured such that the strip port includes a current connector and predetermined control lines that may be configured to measure the resistance values coded on the test strips. More specifically, in one embodiment, the expiration dates may be coded using the resistance value on the wake-up bar in a logical sequence such as follows:

| Resistance Value | Expiration Date |
|---|---|
| 300-310 kOhm | Q1 of odd year |
| 315-320 kOhm | Q2 of odd year |
| ... | |
| 350-360 kOhm | Q1 of even year |

Referring to FIGS. 9A-9C, it can be seen that the wavy lines may increase in thickness or length to change the resistance on the test strip. Furthermore, the pads on the test strip are shown to make contact with the wake-up bar on the strip port. By way of an example, FIG. 9A illustrates 300 KOhm trace width, FIG. 9B illustrates 315 KOhm trace width, and FIG. 9C illustrates 350 KOhm trace width, each associated with a predefined expiration date as described above.

In this manner, in one embodiment of the present disclosure, expiration date of test strips may be automatically detected so that the user is notified of expired date of a given test strip before it used to test for blood glucose levels. Moreover, while the automatic expiration detection is described in conjunction with test strip and blood glucose meters, within the scope of the present disclosure, other medical device or consumable items with expiration dates may benefit from the technique described herein.

Accordingly, a method in one aspect of the present disclosure includes detecting a predefined parameter associated with an operational condition of a medical device such as, for example, but not limited to a blood glucose meter, an analyte monitoring device such as continuous glucose monitoring device, or an infusion pump, transmitting a request for time information in response to the predefined parameter detection, and receiving time information in response to the transmitted request.

The method in one aspect may include storing the received time information.

In a further aspect, the method may include updating one or more stored data based on the received time information.

In still another aspect, the method may include retrieving one or more stored data associated with stored time related information, and updating the retrieved one or more stored data based on the received time information, and further, storing the updated retrieved one or more stored data.

The retrieved one or more stored data may include one or more of a blood glucose measurement value, monitored analyte level data, calibration schedule data, or analyte sensor insertion time data.

Further, transmitting the request for time information may be automatically performed in response to the predefined parameter detection.

In still another aspect, the method may include displaying the received time information.

The method may also include receiving confirmation of the received time information.

The time information may include one or more of a time of day information and date information, or other temporal and/or geographical information such as time zone information, location information, GMT data, and the like.

A medical device in accordance with another aspect of the present disclosure includes one or more processing units, and a memory for storing instructions which, when executed by the one or more processing units, causes the one or more processing units to detect a predefined parameter associated with an operational condition of the medical device, to transmit a request for time information in response to the predefined parameter detection, and to receive time information in response to the transmitted request.

The memory for storing instructions which, when executed by the one or more processing units, may cause the one or more processing units to store the received time information.

The memory for storing instructions which, when executed by the one or more processing units, may cause the one or more processing units to update one or more stored data based on the received time information.

The memory for storing instructions which, when executed by the one or more processing units, may cause the one or more processing units to retrieve one or more stored data associated with stored time related information, and to update the retrieved one or more stored data based on the received time information.

Also, the memory for storing instructions which, when executed by the one or more processing units, may cause the one or more processing units to store the updated retrieved one or more stored data.

In one embodiment, the medical device may include an analyte monitoring device, such as a blood glucose meter, a continuous glucose monitoring device, an integrated continuous glucose monitoring device and blood glucose meter, or a controller unit in communication with one or more of the blood glucose meter, the continuous glucose monitoring device or the integrated continuous glucose monitoring device and blood glucose meter.

For example, in one aspect, the medical device may include an in vitro blood glucose meter. Alternatively, the medical device may include a receiver unit or a controller unit in a continuous glucose monitoring system 110 (FIG. 1), which may additionally incorporate a strip port and the corresponding electronic circuitry for processing blood samples from an in vitro test strip.

In still another aspect, the medical device may include an infusion device for infusing medication such as insulin, for example an external infusion pump, an implantable infusion pump, an inhalable medication dispensing unit, or a medication injection device.

The retrieved one or more stored data includes one or more of a blood glucose measurement value, monitored analyte level data, calibration schedule data, or analyte sensor insertion time data, or any other time associated data such as, for example, a medication delivery schedule such as programmed basal profiles in infusion pumps.

Also, the memory for storing instructions which, when executed by the one or more processing units, may cause the one or more processing units to automatically transmit the request for time information in response to the predefined parameter detection.

The device may include a display unit operatively coupled to the one or more processing units, to display the received time information.

The memory for storing instructions which, when executed by the one or more processing units, may cause the one or more processing units to receive confirmation of the received time information.

The one or more of the processing units may include a communication unit configured to transmit the request for time information or to receive time information in response to the transmitted request, or both.

The communication unit may be configured to transmit or receive information using one or more of a Bluetooth® communication protocol, an RF communication protocol, an infrared communication protocol, a Zigbee® communication protocol, an 802.1x communication protocol, or a wireless personal area network protocol.

A medical device in yet another embodiment may include means for detecting a predefined parameter associated with an operational condition of a medical device, means for transmitting a request for time information in response to the predefined parameter detection, and means for receiving time information in response to the transmitted request.

A therapy management system in one embodiment of the present disclosure includes an infusion device including a processing unit configured to perform data processing, and a user interface unit operatively coupled to a processing unit, where the processing unit is configured to detect a location information associated with the infusion device for output to the user interface unit.

The location information in one embodiment is time based.

In one aspect, the location information is associated with a local time information based on the location of the infusion device, where the location information may be received from a global positioning system (GPS) or from another device, such as a mobile telephone, a GPS enabled personal digital assistant, which has received that information from a global positioning system.

In one aspect, a clock unit may be operatively coupled to the processing unit, where the clock unit is configured to dynamically adjust the location information based on the location of the infusion device.

In a further embodiment, the clock unit may include an atomic clock.

The processor unit may be configured to generate a notification associated with the detected location information for output to the user interface unit, where the notification may be output to the user interface unit as one or more of a date information and time information associated with the location of the infusion device.

The processing unit may be configured to retrieve one or more programmed procedures associated with time, where the one or more programmed procedures may include one or more basal profiles, a programmed bolus determination schedule, a time based condition alert.

The time based condition alert may include one or more of a time based reminder associated with the operation of the infusion device. Further, the time based condition alert may include one or more of a time based reminder associated with the condition of the infusion device user.

In a further aspect, the processor unit may be configured to automatically adjust one or more time based functions associated with the operation of the infusion device based on the detected location information.

A method in accordance with another embodiment includes detecting a change in the location information of a therapy management device, comparing the detected change with a stored location information, and executing one or more processes associated with the operation of the therapy management device based on the detected change.

The detected change in the location information may include one of a time zone change, a time standard change, a date change, or combinations thereof.

The one or more processes may include generating a notification associated with the detected change in the location information.

Further, the one or more processes may include modifying one or more programmed time based functions of the therapy management device and which may include one or more of a programmed time based alert, a programmed time based fluid delivery determination; a programmed time based fluid delivery profile, or a programmed time based operational condition of the therapy management device.

In still another aspect, the therapy management device may include one or more of an infusion device or an analyte monitoring unit.

A therapy management system in accordance with still another embodiment of the present disclosure includes an infusion device, and a communication unit operatively coupled to the infusion device over a wireless data network, the communication device configured to transmit a request for synchronization to the infusion device, where the infusion device may be configured to transmit one or more data to the communication unit in response to the received synchronization request.

The wireless data network may be based on one or more of a Bluetooth® communication protocol, an RF communication protocol, an infrared communication protocol, a Zigbee® communication protocol, an 802.1x communication protocol, or a wireless personal area network such as ANT protocol.

In a further aspect, the wireless data network may include one or more of a wireless local area network, or a WiFi network.

The communication unit may be configured to periodically transmit the synchronization request at a predetermined time interval.

Further, the infusion device may be configured to verify the received synchronization request before transmitting the one or more data to the communication unit.

The transmitted one or more data to the communication unit may be encrypted, and also, the communication unit may be configured to decrypt the received one or more encrypted data.

The transmitted one or more data may include one or more information associated with the stored user profile of the infusion device, an operating parameter of the infusion device, or infusion delivery information.

The communication unit may include one or more of an analyte monitoring unit, a personal digital assistant, a mobile telephone, a computer terminal, a server terminal or an additional infusion device.

A system for communicating with an infusion device in still another embodiment of the present disclosure includes a voice enabled device and an infusion device configured to communicate with the voice enabled device using one or more voice signals.

In one aspect, the voice enabled device may include one or more of a telephone set, a mobile telephone, a voice of IP (Internet Protocol) telephone, a voice enabled computing device, or a voice enabled computer terminal.

The infusion device may be configured to initiate a voice enabled communication to the voice enabled device. For example, the infusion device may be integrated with mobile telephone components.

In one aspect, the voice enabled communication may include a telephone call.

The infusion device may be configured to receive one or more voice commands from the voice enabled device, where the infusion device may be configured to process the one or more voice commands to execute one or more associated functions of the infusion device operation.

The one or more associated functions include a bolus dosage determination, a programmable notification, or a temporarily basal dosage determination.

A method in accordance with yet still another embodiment of the present disclosure includes initiating a voice signal based communication from an infusion device, and transmitting a voice signal associated with the operation of the infusion device.

The method may also include receiving a voice signal based request over a communication network, and executing one or more functions associated with the operation of the infusion device based on the received voice signal based request.

The voice signal based communication may include a telephone call.

A therapy management kit in accordance with still yet another embodiment includes an infusion device including a processing unit configured to perform data processing, and a user interface unit operatively coupled to a processing unit, where the processing unit is configured to detect a location information associated with the infusion device for output to the user interface unit.

The kit may further include a clock unit operatively coupled to the processing unit, where the clock unit is configured to dynamically adjust the location information based on the location of the infusion device.

The clock unit may include an atomic clock.

In a further aspect, the kit may also include a voice enabled device, where the infusion device may be further configured to communicate with the voice enabled device using one or more voice signals.

In one aspect, the voice enabled device may include one or more of a telephone set, a mobile telephone, a voice of IP (Internet Protocol) telephone, a voice enabled computing device, or a voice enabled computer terminal.

The various processes described above including the processes performed by the processor 210 in the software application execution environment in the fluid delivery device 120 as well as any other suitable or similar processing units embodied in the analyte monitoring system 120 and the remote terminal 140, including the processes and routines described in conjunction with FIGS. 3-8, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 or the remote terminal 140) of the processor 210, may be developed by a person of ordinary skill in the art and may include one or more computer program products.

In addition, all references cited above herein, in addition to the background and summary of the invention sections, are hereby incorporated by reference into the detailed description of the preferred embodiments as disclosing alternative embodiments and components.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A method, comprising:
   transmitting, from a medical device, a request for time information over a communication channel;
   receiving, at the medical device, a time information in response to the transmitted request;
   updating data stored in the medical device based on the received time information;
   determining, with one or more processors, a resistance for a component associated with the medical device;
   matching, with the one or more processors, the determined resistance to a corresponding stored value, the stored value associated with an expiration date of the component associated with the medical device;
   determining, with the one or more processors, the expiration date of the component based on the received time information and the determined resistance; and
   generating, with the one or more processors, an output signal based on the determined expiration date.

2. The method of claim 1, wherein the updated stored data includes one or more parameters associated with a programmed medication delivery profile.

3. The method of claim 1, wherein transmitting the request for time information includes automatically transmitting the request for time information upon detection of a time zone change associated with the medical device.

4. The method of claim 1, further including receiving confirmation of the received time information.

5. The method of claim 1, wherein the time information includes one or more of a time of day information or date information.

6. The method of claim 1, wherein transmitting the request for time information includes automatically transmitting the request upon detection of an operational condition, the operational condition corresponding to one or more of delivering a medication to a patient, transferring data from the medical device to a secondary device, or powering on the medical device.

7. The method of claim 1, further comprising modifying a preprogrammed time based medication delivery profile based on the received time information.

8. The method of claim 7, further comprising obtaining confirmation of the modification prior to implementing the modification to the preprogrammed time based medication delivery profile.

9. The method of claim 1, wherein the component includes one or more of a blood glucose test strip or an infusion set.

10. The method of claim 1, further comprising:
    initiating local synchronization between the medical device and a secondary device;
    verifying an identity of the secondary device;
    approving synchronization between the medical device and the secondary device; and
    synchronizing the medical device with the secondary device.

11. A medical device, comprising:
    one or more processing units; and
    a memory for storing instructions which, when executed by the one or more processing units, causes the one or more processing units to transmit a request for time information over a communication channel, receive a time information in response to the transmitted request, update data stored in the medical device based on the received time information, determine a resistance for a component associated with the medical device, match the determined resistance to a corresponding stored value, the stored value associated with an expiration date of the component associated with the medical device, determine the expiration date of the component based on the received time information and the determined resistance, and generate an output signal based on the determined expiration date.

12. The medical device of claim 11, wherein the updated stored data includes one or more parameters associated with a programmed medication delivery profile.

13. The medical device of claim 11, wherein the instructions to transmit the request for time information includes instructions to automatically transmit the request for time information upon detection of a time zone change associated with the medical device.

14. The medical device of claim 11, further including instructions which, when executed by the one or more processing units, causes the one or more processing units to receive confirmation of the received time information.

15. The medical device of claim 11, wherein the time information includes one or more of a time of day information or date information.

16. The medical device of claim 11, wherein the instructions to transmit the request for time information includes instructions to automatically transmit the request upon detection of an operational condition, the operational condition corresponding to one or more of delivering a medication to a patient, transferring data from the medical device to a secondary device, or powering on the medical device.

17. The medical device of claim 11, further comprising instructions which, when executed by the one or more processing units, causes the one or more processing units to modify a preprogrammed time based medication delivery profile based on the received time information.

18. The medical device of claim 17, further comprising instructions which, when executed by the one or more processing units, causes the one or more processing units to obtain confirmation of the modification prior to implementing the modification to the preprogrammed time based medication delivery profile.

19. The medical device of claim 11, wherein the component includes one or more of a blood glucose test strip, or an infusion set.

20. The medical device of claim 11, further comprising instructions which, when executed by the one or more processing units, causes the one or more processing units to initiate local synchronization between the medical device and a secondary device, verify an identity of the secondary device, approve synchronization between the medical device and the secondary device, and synchronize the medical device with the secondary device.

* * * * *